United States Patent
Shaw et al.

[11] Patent Number: 5,377,533
[45] Date of Patent: Jan. 3, 1995

[54] METHOD OF TAKING EROSION/CORROSION MEASUREMENTS

[76] Inventors: Larry Shaw, RR#1, Lepreau, New Brunswick, Canada, E0G 2H0; William Perrin, RR#1, Lepreau, New Brunswick, Canada, E3B 1C4

[21] Appl. No.: 972,406

[22] Filed: Nov. 6, 1992

[30] Foreign Application Priority Data

Jul. 20, 1992 [CA] Canada .................. 2074239

[51] Int. Cl.⁵ .................................. G01N 17/00
[52] U.S. Cl. ................................. 73/86; 422/53
[58] Field of Search ................. 73/86; 422/53; 33/543.1, 544, 562, 563, 566

[56] References Cited

U.S. PATENT DOCUMENTS

| | | | |
|---|---|---|---|
| 3,827,290 | 8/1974 | Carlson | 73/86 |
| 4,605,065 | 8/1986 | Abererombie | 73/86 X |
| 5,069,774 | 12/1991 | Hladky et al. | 204/404 |
| 5,100,780 | 3/1992 | Haslbeck et al. | 422/53 X |
| 5,170,661 | 12/1992 | Lewis et al. | 73/61.62 |
| 5,243,850 | 9/1993 | Hanson | 73/86 |

OTHER PUBLICATIONS

*Patent Abstracts of Japan;* "Corrosion Resistance Diagnotic Device of In-Core Structure Material" (3-252591) Grp. p. 1309, vol. 16, No. 53, Abs pub. Feb. 10, 1992.
"Device for Diagnosing Corrosion Resistance of In-- Pile Structural Material" (3-4145) Grp p. 1181, vol. 15, No. 115, Abs pub. Mar. 19, 1991.
"Detection of Damage of Apparatus for High Temperature" (2-28544), Grp. p. 1034, vol. 14, No. 179, Abs pub. Apr. 10, 1990.
Investigation for Corrosion of Submarine Pipe (58-2643) ABS Grp. p. 186, vol. 7, No. 73, Abs pub. date Mar. 25, 1983.

*Primary Examiner*—Tom Noland
*Attorney, Agent, or Firm*—Jeffrey T. Imai; Arne I. Fors; D. Doak Horne

[57] ABSTRACT

A method of taking erosion/corrosion measurements of a piping system for logging a history of the piping system over time comprises the steps of: (a) Wrapping a template about the pipe component; (b) Aligning the template with a reference marking on the pipe component; (c) Taking a wall thickness measurement at each of the spaced holes; (d) Recording at least the wall thickness measurement at each of the spaced holes and the indicia of the spaced hole location. The template extends circumferentially about the pipe component and has a plurality of spaced holes arranged in a grid pattern which holes extend through the template for receiving a probe for measuring wall thickness of the pipe component. The template has indicia for identifying each of the spaced holes.

6 Claims, 3 Drawing Sheets

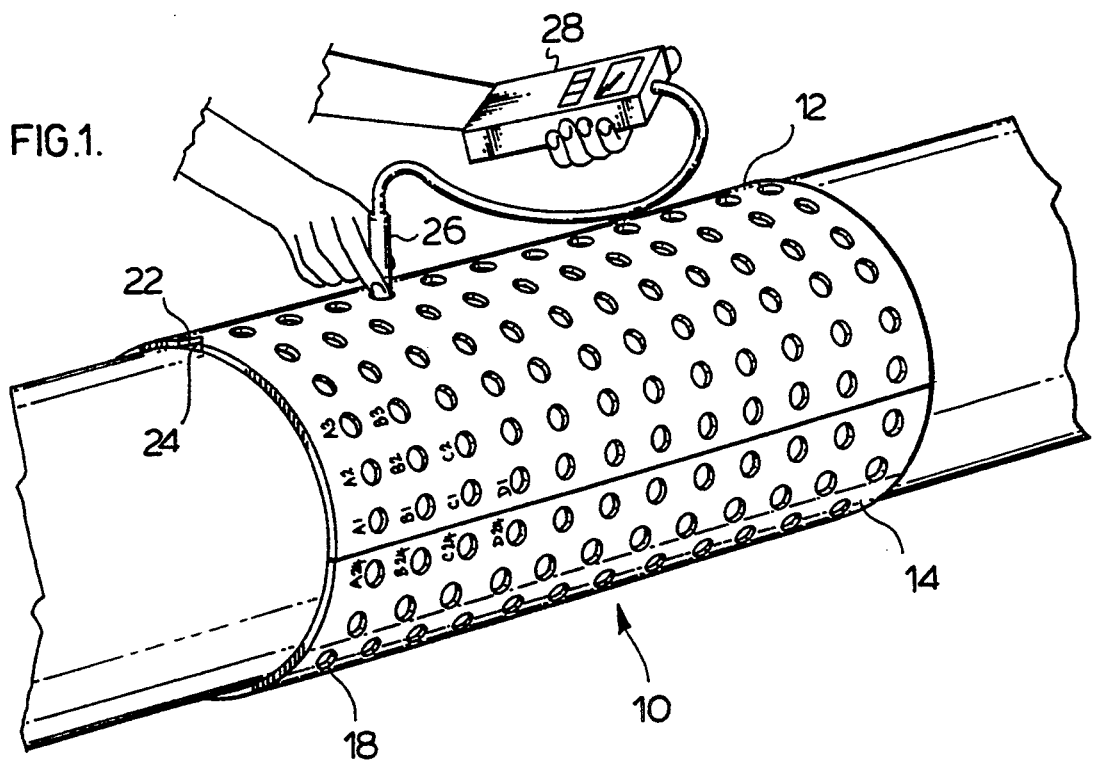
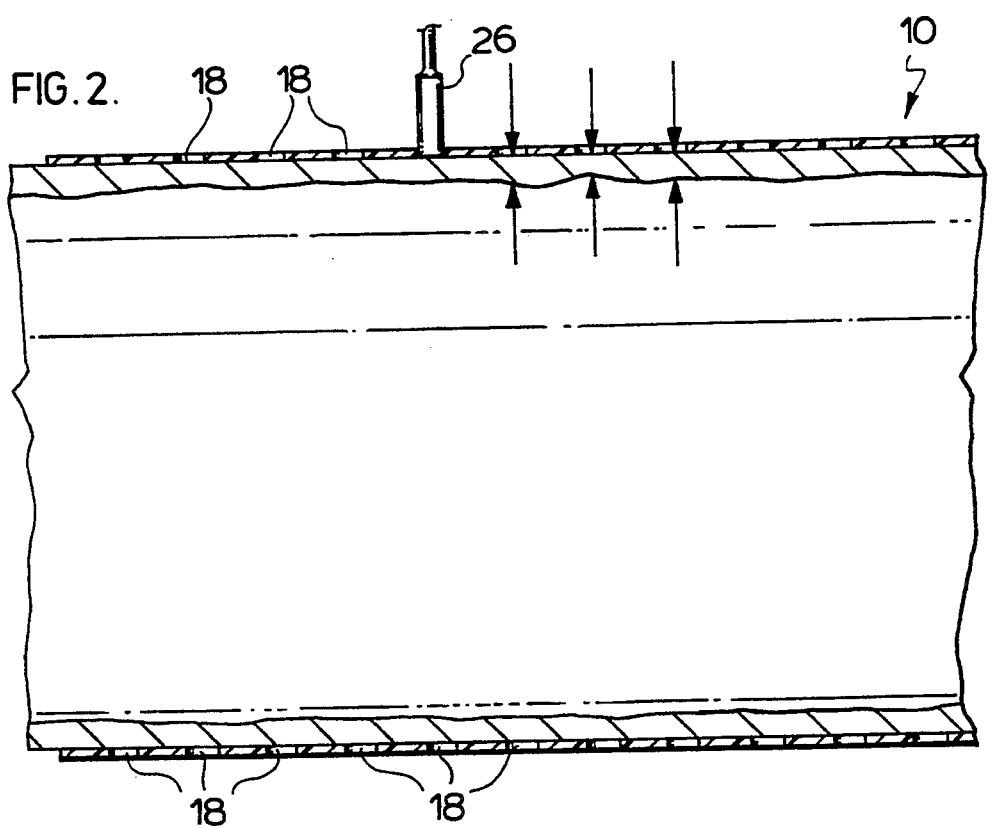

METHOD OF TAKING EROSION/CORROSION MEASUREMENTS

FIELD OF INVENTION

This invention relates to a method of apparatus for taking erosion and corrosion measurements of high pressure piping systems. In particular, this invention relates to the use of a template for taking consistent measurements for charting the history of a piping system over time.

BACKGROUND OF INVENTION

In industrial plants, piping systems for boilers, steam lines, liquid chemicals and the like are used to transport the materials from one location to another. The materials can be highly corrosive to the piping or can be transported under high temperatures and pressures which will cause extensive wear to the piping. Failure of the piping systems can be catastrophic in many instances, both in terms of environmental concerns and in terms of unscheduled emergency down time for a plant.

Accordingly, systems have been developed to record the history of wear on the piping. A hand-held ultra-sonic thickness gauge has been developed for on-site data logging. The ultra-sonic gauge will measure the thickness of a pipe wall and record the measurement data in a memory together with other relevant information such as temperature, reading location and conversion. The data is downloaded onto a personal computer which then processes the data into an effective maintenance schedule and history of the plant piping system. Such systems are available under the trademark DML DL by KRAUTKRAMER BRANSON.

In order to obtain an accurate history of measurements taken from the piping systems, the measurements must be taken from the same location so that wear from corrosion or erosion can be identified. If the measurements are not taken from the same location, false readings can be obtained which may result in accelerated repair schedules.

The most common method of taking same location measurements is to place a grid pattern on the pipe component. The outside area of the pipe component is divided into a grid pattern. The size of the grid pattern can vary but many industries, such as nuclear utilities, have standardized the sizes. Grid sizes can vary from 1 to 6 inches (2.54 to 21.24 cm), depending on the size of the component which can vary from 2 to 30 inches (5.08 to 76.2 cm).

To commence an inspection, two persons normally will measure and draw the grid pattern on the component. A marker, paint, sticker or other marking device is used to scribe lines circumferentially around the component and axially along the length of the component. The spacing between all lines is maintained to as near the designated grid size as possible. Normally, it takes 6 to 20 person hours of labour to lay out and draw the grid lines.

Once the grid lines are in place, the inspection can take place. An ultra-sonic probe takes a thickness measurement where the lines intersect. The data is stored for later analysis by the computer.

A second method which is used is to place thin strips of a width of a corresponding grid size about the circumference of the component. The strips have a series of spaced holes ½ to ¼ inch (1.27 to 0.635 cm) corresponding to the grid size used. Two persons place the strips about the component, attempting to maintain the grid size. As the strip is placed in the proper position, the hole positions are marked on the component using markers or spray paint. The strips are removed and then the readings using an ultra-sonic probe are taken and processed.

Both of these methods are prone to errors in the layout of the grid and also of the inspectors in taking the readings. The inspector is required to trace each grid line or painted dot back to a starting reference point to determine the identification of the inspection point being measured. This results in the consumption of considerable inspection time which results in data which is not very accurate when repeating the inspection for a determination of wall losses at a future date.

Further, it is quite common for the grid markings or painted dots to be missing for future inspections. Remarking is then required, which remarking is never in the exact location as the previous markings.

SUMMARY OF THE INVENTION

The disadvantages of the prior art is overcome by providing a method of taking accurate and consistent erosion/corrosion measurements by using a template having pre-drilled holes through which measurements are taken.

It is further desirable to have a method of taking erosion/corrosion measurements where each location is identified for accurate recordal of measurement data.

It is further desirable to have a method of taking erosion/corrosion measurements are repeated over a period of time at the exact location to provide an accurate history of the erosion/corrosion rate of wall thickness reduction.

It is further desirable to have a method of taking erosion/corrosion measurements in a quick and efficient manner.

According to one aspect of the invention, there is provided a method of taking erosion/corrosion measurements of a piping system for logging a history of the piping system over time, comprising the steps of:

(a) Wrapping a template about the pipe component. The template extends circumferentially about the pipe component and has a plurality of spaced holes arranged in a grid pattern which holes extend through said template for receiving a probe for measuring wall thickness of said pipe component. The template has indicia for identifying each of the spaced holes.

(b) Aligning the template with a reference marking on the pipe component.

(c) Taking a wall thickness measurement at each of the spaced holes.

(d) Recording at least the wall thickness measurement at each of the spaced holes and the indicia of the spaced hole location.

In a further aspect, the method includes the step of repeating steps (a) through (d) over a predetermined period of time to log the history of wear of the pipe component.

In a further aspect, a template is provided for taking erosion and corrosion measurements of a piping system for logging a history of the piping system over time. The template comprises a first half and a second half section adapted to wrap circumferentially about a pipe component of said piping system. The template has a plurality of spaced holes arranged in a grid pattern. The holes extend through the template for receiving a probe for measuring wall thickness of the pipe component. The template has indicia for identifying each of the spaced holes and has a reference marking for aligning the template with a reference marking on the pipe component.

In a further aspect, the template is made from a material capable of withstanding temperatures of about 180° C., preferably fiber glass.

In a further aspect, the template has a first and second half faces releasably securable to the piping component and extending circumferentially thereabout.

DESCRIPTION OF THE DRAWINGS

In drawing which illustrate the embodiment of the invention,

FIG. 1 is perspective view of the template of the invention positioned about a straight piping and thickness measurements being taken and recorded;

FIG. 2 is sectional view along the longitudinal extent of a piping with template of the invention of FIG. 1 wrapped thereabout;

DETAILED DESCRIPTION OF THE INVENTION

Figure 3:
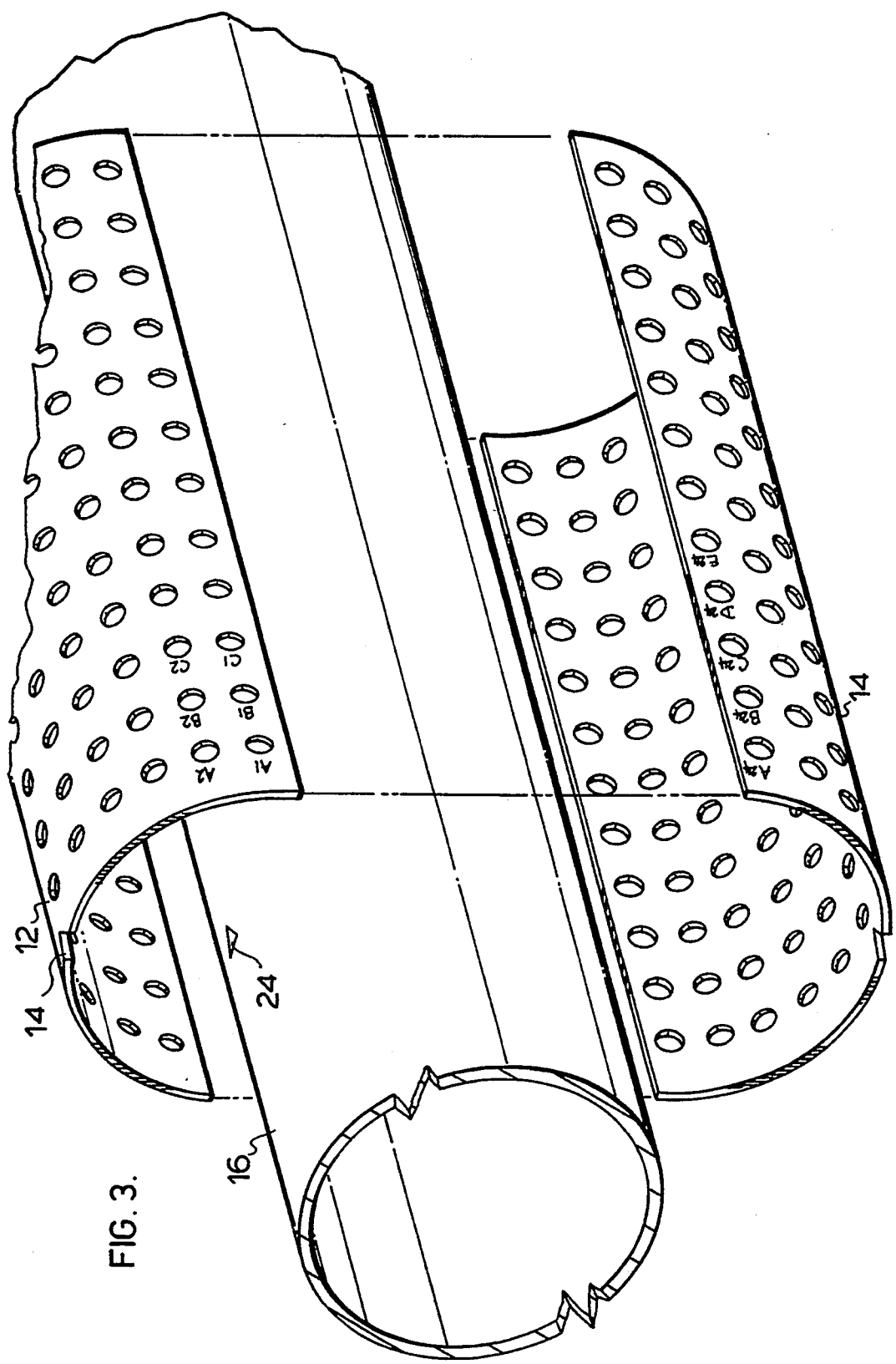
FIG. 3 is a perspective exploded view of the template of the invention being positioned about a straight section of pipe.

The template of the present invention is illustrated in FIG. 1 as 10. Template 10 comprises a first half 12 and second half 14. First half 12 and second half 14 mate with each other to fully surround the circumference of pipe 16. Template 10 can be of any length depending on the available space of piping 16 which is to be measured.

The template 10 has an array of holes 18 extending through the thickness of the template 10. The array of holes is arranged in a grid pattern. The distance between holes or the grid size can be any distance provided the holes are spaced uniformly in both the axial and circumferential direction. Normally a grid size will vary from 1 to 6 inches (2.54 to 21.24 cm), depending on the length of the component which can vary from 2 to 30 inches (5.08 to 76.2 cm). Alternatively, a special grid size could be used on particular pipe components.

Each hole has an indicia 20 to identify each hole. In this case, an alphabet letter is used to identify the axial position of the hole, while a numeral is used to indicate the circumferential position of the hole. Any method of coding the hole position would be suitable provided the data was being recorded and can be consistently processed to establish a history of the piping component.

Second half 12 has a reference notch 22 at one end. Pipe 16 will have a reference mark 24 on the outer surface. Reference mark 24 can be any permanent mark on the pipe, such as a paint mark or a casted protrusion. Reference notch 22 is aligned with reference mark 24 to accurately re-install template 10 onto pipe 16.

Figure 4:
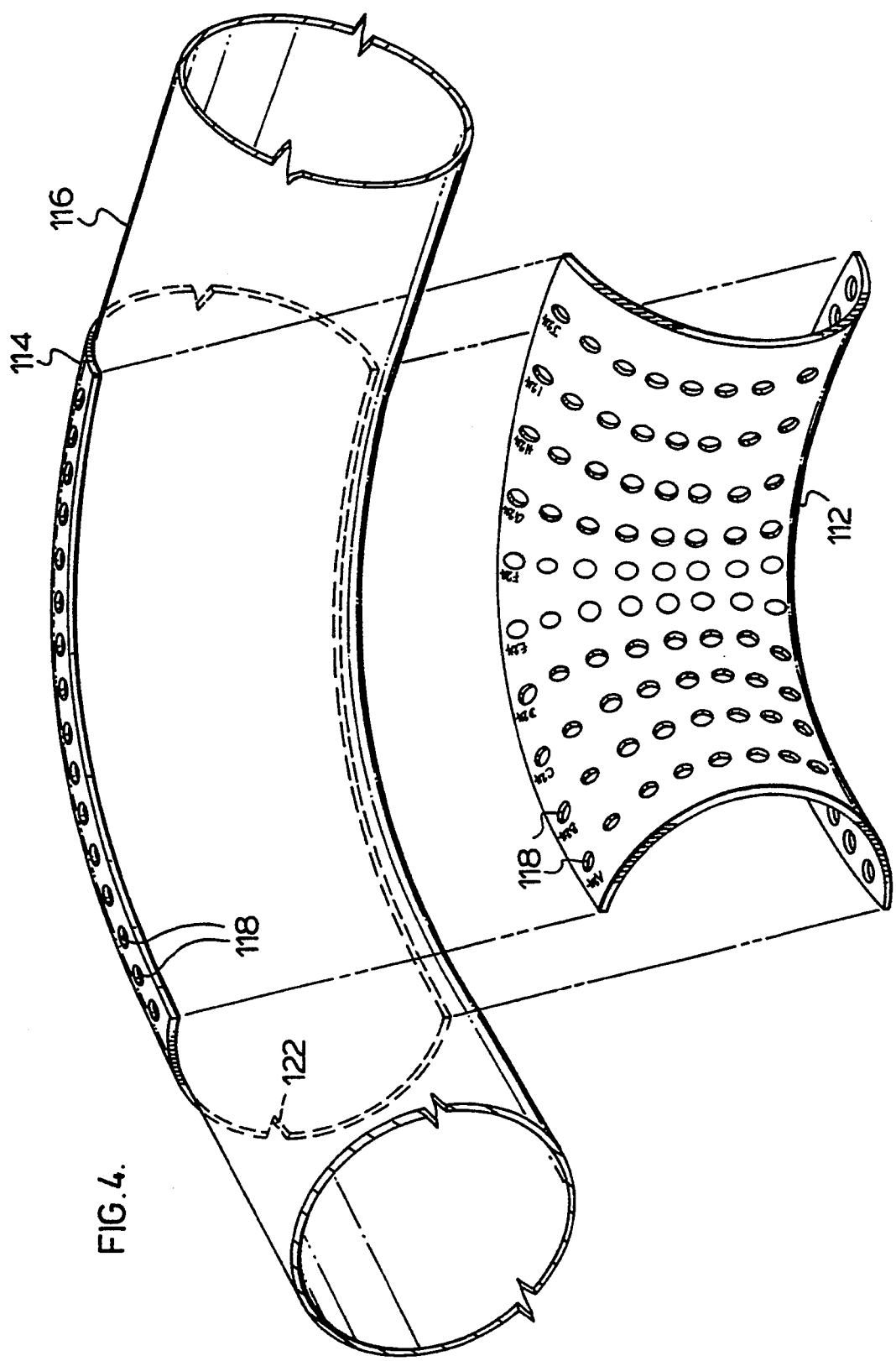
FIG. 4 is a perspective exploded view of a template of the invention contoured for an elbow joint piping.

In FIG. 4, the template is illustrated as being arcuate in shape for fitting with an elbow shaped pipe component 116. The template comprises first half 112 and second half 114 and having a plurality of holes 118 aligned in a grid pattern. Each hole 118 is marked with indicia in the same manner as the straight template 10.

In the preferred embodiment, template 10 is made from a fiber glass material. Any suitable material may be used. However for high temperature piping systems, the template must be able to withstand temperatures in excess of 180° C. Fiberglass is advantageous being light weight, rugged, durable and will not break under normal industrial use. Further, the smooth finish allows easy removal of couplants and contamination products. Fiber glass does not require heated storage and is not affected by weather or chemicals.

In use, pipe component 16 is marked with a reference mark 24, if the pipe does not already include such a mark. Template halves 12 and 14 are wrapped about pipe component 16 and releasably secured to each other to extend circumferentially about pipe component 16. The reference notch 22 of template 10 is aligned with reference marking 24. A plurality of spaced holes 18 arranged in a grid pattern extend about the circumference of the pipe component 16. A probe 26 for measuring wall thickness of the pipe component 16 is placed in one of the holes until it contacts the wall of pipe component 16. The template has indicia for identifying each of the spaced holes. Wall thickness measurements are taken at each of the spaced holes.

The wall thickness measurement at each of the spaced holes and the indicia of the spaced hole location are recorded on a site file of an on-site data logger 28.

The recorded data from the data logger 28 is then downloaded onto a personal computer which processes the data to create a history of the piping component. The history may be analyzed to form the basis to schedule routine maintenance on and replacement of the piping components.

Alternatively, the thickness measurements and the location codes can be recorded manually on a manual recording report.

The method of the present invention greatly reduces the time required for taking accurate thickness measurements. Due to the simplicity of the template, it may be installed and removed very quickly and easily. The possibility that an inspector will take improper readings is greatly reduced as the inspector does not have to continually identify grid lines. The measuring locations remain consistent from year to year and insures repeatability when inspection staff are changed.

The above description relates to the preferred method by way of example only. Many variations on the invention will be obvious to those knowledgeable in the field, and such obvious variations are within the scope of the invention, whether or not expressly described.

I claim:

1. A method of taking erosion and corrosion measurements of a piping system for logging a history of the piping system over time, comprising the steps of:
   (a) wrapping a template about a pipe component, said template adapted to circumferentially extend about said pipe component, said template having a plurality of spaced holes arranged in a grid pattern which extend through said template for receiving a probe for measuring wall thickness of said pipe component, said template having indicia for identifying each of said spaced holes;
   (b) aligning said template with a reference marking fixed on said pipe component;
   (c) taking a wall thickness measurement at each of said spaced holes;
   (d) recording at least said wall thickness measurement at each of said spaced holes and said indicia of said spaced hole location.

2. A method as claimed in claim 1 wherein said method further includes the step of repeating steps (a) through (d) over a predetermined period of time to log the history of wear of the pipe component.

3. A method as claimed in claim 1 wherein said method includes the initial step of marking said pipe component with said reference marking.

4. A method as claimed in claim 3 wherein said template includes a reference notch for aligning with said reference marking on said pipe component.

5. A method as claimed in claim 4 wherein said template is made from a material capable of withstanding temperatures of about 180° C.

6. A method as claimed in claim 5 wherein said material is a fiber glass.

* * * * *